United States Patent
Gupta et al.

(10) Patent No.: US 11,674,870 B2
(45) Date of Patent: *Jun. 13, 2023

(54) SAMPLE PROTECTION METHOD

(71) Applicants: Bipin Gupta, Pleasanton, CA (US); Marc Key, Ojai, CA (US)

(72) Inventors: Bipin Gupta, Pleasanton, CA (US); Marc Key, Ojai, CA (US)

(73) Assignees: Diagnostic BioSystems, Pleasanton, CA (US); Marc Key, Ojai, CA (US)

( * ) Notice: Subject to any disclaimer, the term of this patent is extended or adjusted under 35 U.S.C. 154(b) by 652 days.

This patent is subject to a terminal disclaimer.

(21) Appl. No.: 16/750,148

(22) Filed: Jan. 23, 2020

(65) Prior Publication Data
US 2021/0055189 A1 Feb. 25, 2021

Related U.S. Application Data

(60) Provisional application No. 62/888,822, filed on Aug. 19, 2019.

(51) Int. Cl.
*G01N 1/30* (2006.01)
*G01N 1/28* (2006.01)
(Continued)

(52) U.S. Cl.
CPC ........... *G01N 1/30* (2013.01); *C08G 65/3326* (2013.01); *C08L 29/04* (2013.01); *C08L 71/02* (2013.01); *C09D 105/04* (2013.01); *C09D 129/04* (2013.01); *C09D 171/02* (2013.01); *G01N 1/28* (2013.01); *G01N 1/2813* (2013.01);
(Continued)

(58) Field of Classification Search
CPC ................ G01N 2001/302; G01N 2001/305
See application file for complete search history.

(56) References Cited

FOREIGN PATENT DOCUMENTS

WO WO-0159164 A1 * 8/2001 ............... G01N 1/30

OTHER PUBLICATIONS

Yamashita, Shuji, "Heat-induced antigen retrieval: Mechanisms and application to histochemistry", Progress in Histochemistry and Cytochemistry, vol. 41, pp. 141-200. (Year: 2007).*

* cited by examiner

*Primary Examiner* — Michelle F. Paguio Prising
*Assistant Examiner* — Grant C Currens
(74) *Attorney, Agent, or Firm* — PatentFile, LLC; Bradley C. Fach; Steven R. Kick

(57) ABSTRACT

A sample protection method is provided which may be used for protecting a biological sample on a microscope slide, such as during heat-induced target retrieval and/or after heat-induced target retrieval such that: 1) the sample remains adherent to the microscope slide; and 2) the microscopic morphology of the biological sample remains intact. In some embodiments, the sample protection method may include the steps of: creating a sectioned sample that is in contact with a microscope slide; applying a protecting reagent onto a sectioned sample that is in contact with a microscope slide and drying the protecting reagent in which the protecting reagent may be both applied and dried onto the sectioned sample before and/or after performing target retrieval on the sectioned sample. The protecting reagent may include a water-soluble polymer and/or a water-soluble wax, such as polyethylene glycol, polypropylene glycol, polyvinyl alcohol, polyvinylpyrrolidone, alginic acid, and carrageenan.

10 Claims, 5 Drawing Sheets

(51) Int. Cl.
*G01N 33/483* (2006.01)
*G01N 1/44* (2006.01)
*C08G 65/332* (2006.01)
*G01N 1/42* (2006.01)
*C09D 171/02* (2006.01)
*C09D 129/04* (2006.01)
*C09D 105/04* (2006.01)
*G02B 21/34* (2006.01)
*C08L 71/02* (2006.01)
*C08L 29/04* (2006.01)

(52) U.S. Cl.
CPC ................. *G01N 1/42* (2013.01); *G01N 1/44* (2013.01); *G01N 33/4833* (2013.01); *G01N 2001/302* (2013.01); *G02B 21/34* (2013.01)

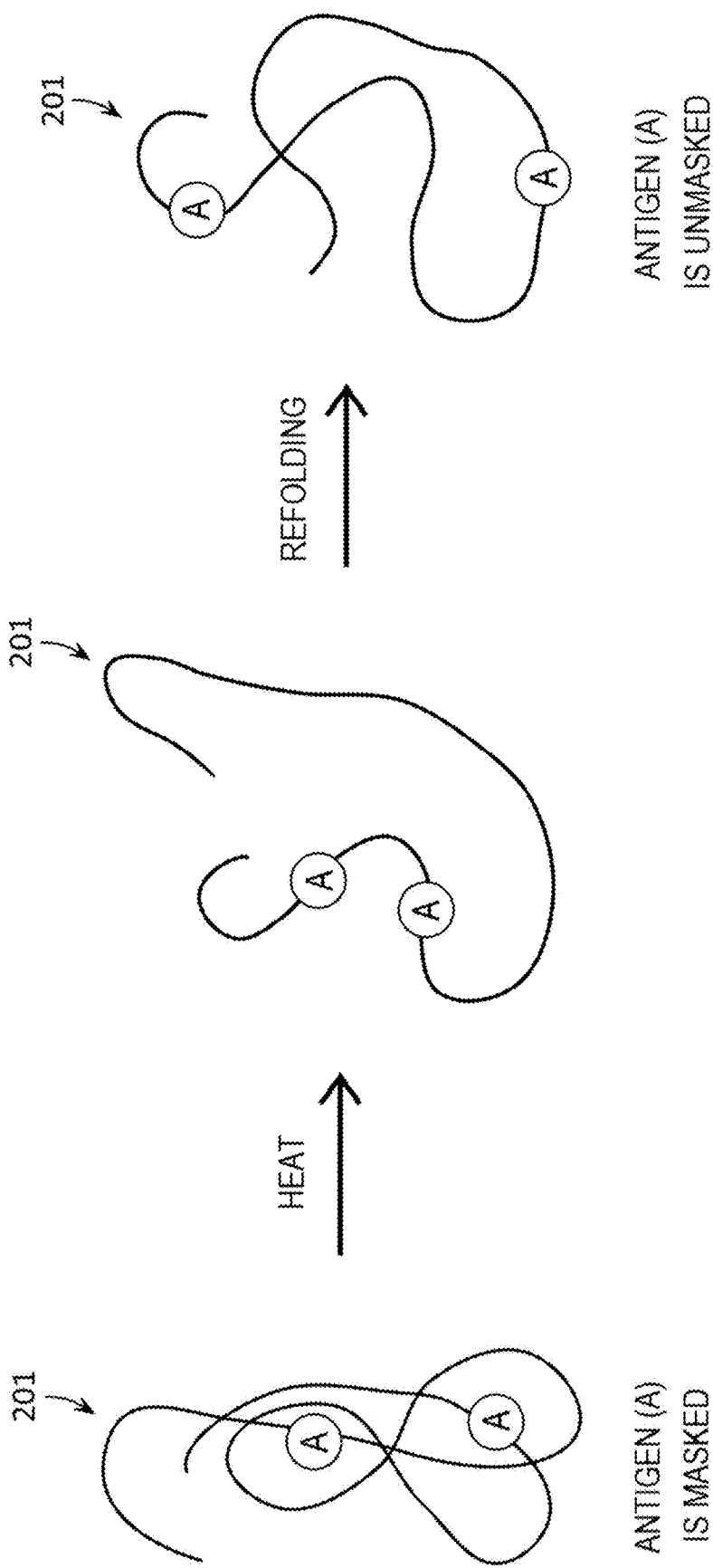

SAMPLE PROTECTION METHOD

CROSS REFERENCE TO RELATED APPLICATIONS

This application claims priority to and the benefit of the filing date of U.S. Provisional Application No. 62/888,822, filed on Aug. 19, 2019, entitled "SAMPLE PROTECTION DURING HEAT PROCESSING", which is hereby incorporated by reference in its entirety.

FIELD OF THE INVENTION

This patent specification relates to the field of biological sample protection methods. More specifically, this patent specification relates to a method of protecting a biological sample during various microscopy analysis procedures.

BACKGROUND

Biological samples of cells and/or tissues are obtained for purposes of analyzing the biological constituents that comprise the sample. Sample analysis may be performed by methods of immunohistochemistry for analyzing protein components, or in situ hybridization for analyzing nucleic acid components. Prior to the analysis the sample must be prepared by appropriate methods.

Sample detachment from a microscope slide is a common problem encountered in histological sample analysis. Microscope slide manufacturers commonly treat the microscope slides to impart an electrostatic charge to the microscope slide. Such slides may be referred to as positively charged or negatively charged slides, depending on the charges incorporated onto the slide. These electrostatic charges have the ability to bind samples more firmly. However, even these enhancements are not entirely effective in retaining samples during heat-treatment.

Additionally, antigen retrieval solutions frequently have a specific pH. These can be generally classified as acidic (pH 2-5), neutral (pH 6-7), or basic pH 8-9). The pH of the antigen retrieval solution also influences sample adherence. Basic antigen retrieval solutions (pH 8-9) are more prone to causing sample detachment compared to the neutral or acidic antigen retrieval solutions.

Furthermore, composition of the sample also influences sample adherence. Tissue samples comprised of abundant fatty material are more prone to detachment compared to less fatty tissues.

All of these factors, microscope slide, antigen-retrieval composition, and sample composition, decrease sample adherence to the microscope slide. Thus far, none of the improvements or modifications to the antigen retrieval method or the microscope slide have been completely satisfactory in retaining a sample on a microscope slide during heat treatment. Other methods that have attempted to overcome this problem have focused on the composition and structure of the microscope slide. Various microscope slides have been introduced that contain an electrostatic charge (either positively or negatively charged). These charged slides interact with opposite charges in the biological sample to help affix the sample onto the microscope slide. Other methods of modifying the microscope slide include applying various coatings such as poly-1-lysine or silane, which likewise introduces charges onto the surface of the microscope slide.

After a sample is sectioned and the thin section is applied to the slide, the sample will firmly bind due to the electrostatic charges. In many cases this binding is sufficient to maintain the sample affixed to the slide during heat-induced antigen retrieval, but in other cases the sample still detaches from the slide during heat-induced antigen retrieval despite these modifications to the microscope slide. Therefore, a need exists for novel methods for adhering a sample to a microscope slide and protecting the sample during heat processing. Furthermore, a need exists for methods of protecting a sample during heat treatment which may be combined with other methods, such as charged microscope slides.

BRIEF SUMMARY OF THE INVENTION

A sample protection method is provided which may be used for protecting a biological sample on a microscope slide, such as during target retrieval and/or after target retrieval such that: 1) the sample remains adherent to the microscope slide; and 2) the microscopic morphology of the biological sample remains intact.

In some embodiments, the sample protection method may include the steps of: applying a protecting reagent onto a sectioned sample that is in contact with a microscope slide; drying the protecting reagent; and performing target retrieval on the sectioned sample.

In further embodiments, the sample protection method may include the steps of: creating a sectioned sample that is in contact with a microscope slide; applying a protecting reagent onto the sectioned sample; drying the protecting reagent; and performing target retrieval on the sectioned sample.

In further embodiments, the sample protection method may include the steps of: performing target retrieval on the sectioned sample that is in contact with a microscope slide; applying a protecting reagent onto the sectioned sample; and drying the protecting reagent.

In further embodiments, the sample protection method may include the steps of: creating a sectioned sample that is in contact with a microscope slide; performing target retrieval on the sectioned sample; applying a protecting reagent onto the sectioned sample; and drying the protecting reagent.

In still further embodiments, the protecting reagent may include a water-soluble wax and/or a water-soluble polymer.

In still further embodiments, the protecting reagent may include a water-soluble wax dissolved in water and/or a water-soluble polymer dissolved in water.

In still further embodiments, the protecting reagent may comprise polyethylene glycol, polyvinyl alcohol, polyvinylpyrrolidone, alginic acid, and/or carrageenan.

The method of the present invention comprises numerous objects, features and advantages that will be readily apparent to those of ordinary skill in the art.

It is an object of the present invention to provide a method and a composition for protecting a biological sample from damage during heat processes.

Another object is to provide a method and a composition for protection of a biological sample from incurring damage caused by heat-induced antigen retrieval prior to immunohistochemical staining.

Another object is to provide a method and a composition for protection of a biological sample from incurring damage caused by heat-induced target retrieval prior to In Situ Hybridization staining.

Another object is to provide a method and a composition for protecting a sample during target retrieval that prevents the sample from detaching from a microscope slide.

Another object is to provide a method and a composition for protecting a sample during target retrieval that prevents damage to sample structure and retains tissue and cellular morphology as viewed microscopically.

BRIEF DESCRIPTION OF THE DRAWINGS

Some embodiments of the present invention are illustrated as an example and are not limited by the figures of the accompanying drawings, in which like references may indicate similar elements and in which:

FIG. 2-FIG. 2 illustrates a diagram of heat induced antigen retrieval type target retrieval which may be used in some embodiments of a sample protection method according to various embodiments described herein.

DETAILED DESCRIPTION OF THE INVENTION

Figure 1A:
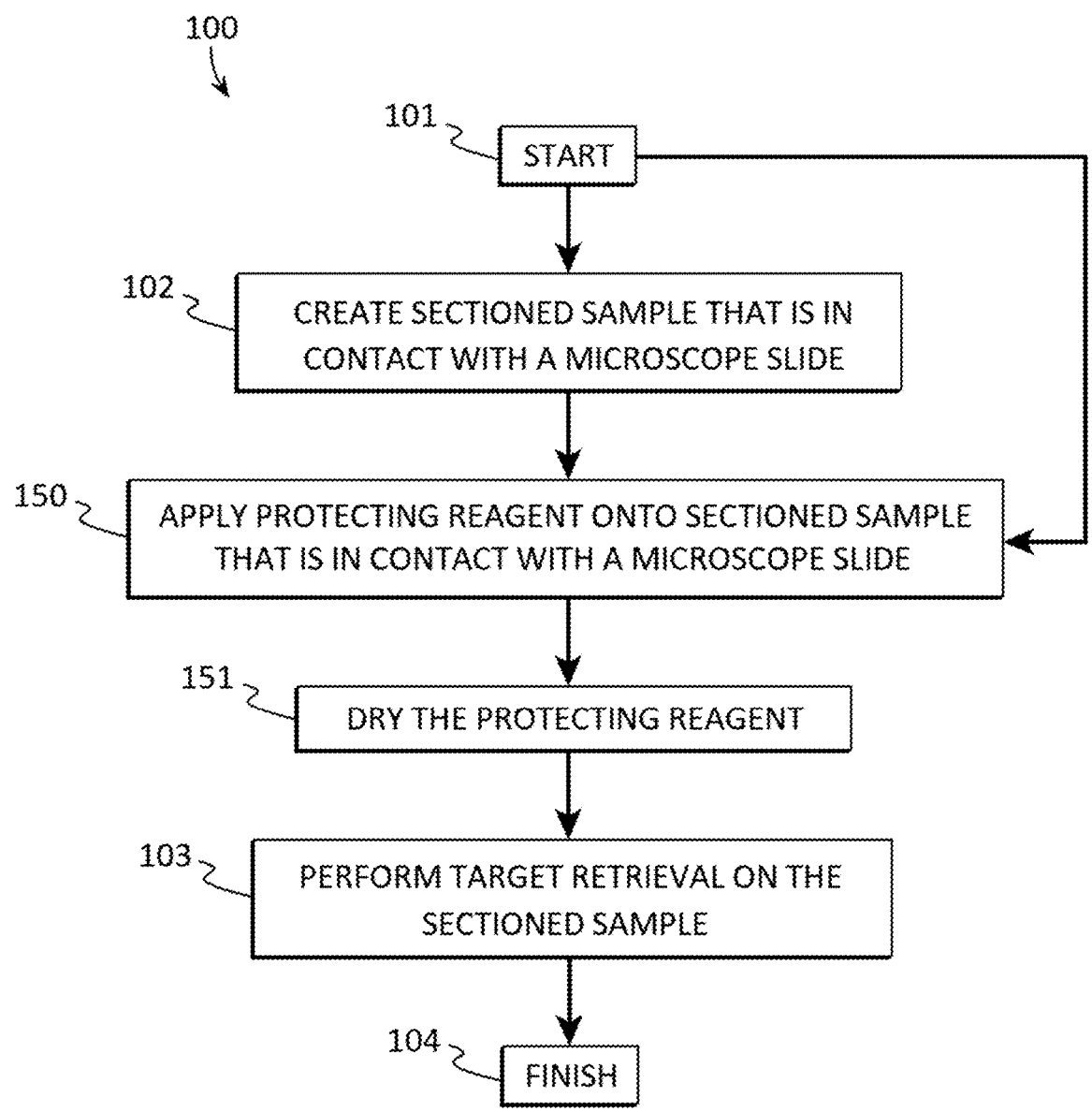
FIG. 1A-FIG. 1A depicts a block diagram of an example of a sample protection method according to various embodiments described herein.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

For purposes of description herein, the terms "upper", "lower", "left", "right", "rear", "front", "side", "vertical", "horizontal", and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As used in this application, the term "about" or "approximately" refers to a range of values within plus or minus 10% of the specified number. Additionally, as used in this application, the term "substantially" means that the actual value is within about 10% of the actual desired value, particularly within about 5% of the actual desired value and especially within about 1% of the actual desired value of any variable, element or limit set forth herein.

A new sample protection method is discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention and is not intended to limit the invention to the specific embodiments illustrated by the figures or description below.

Figure 1B:
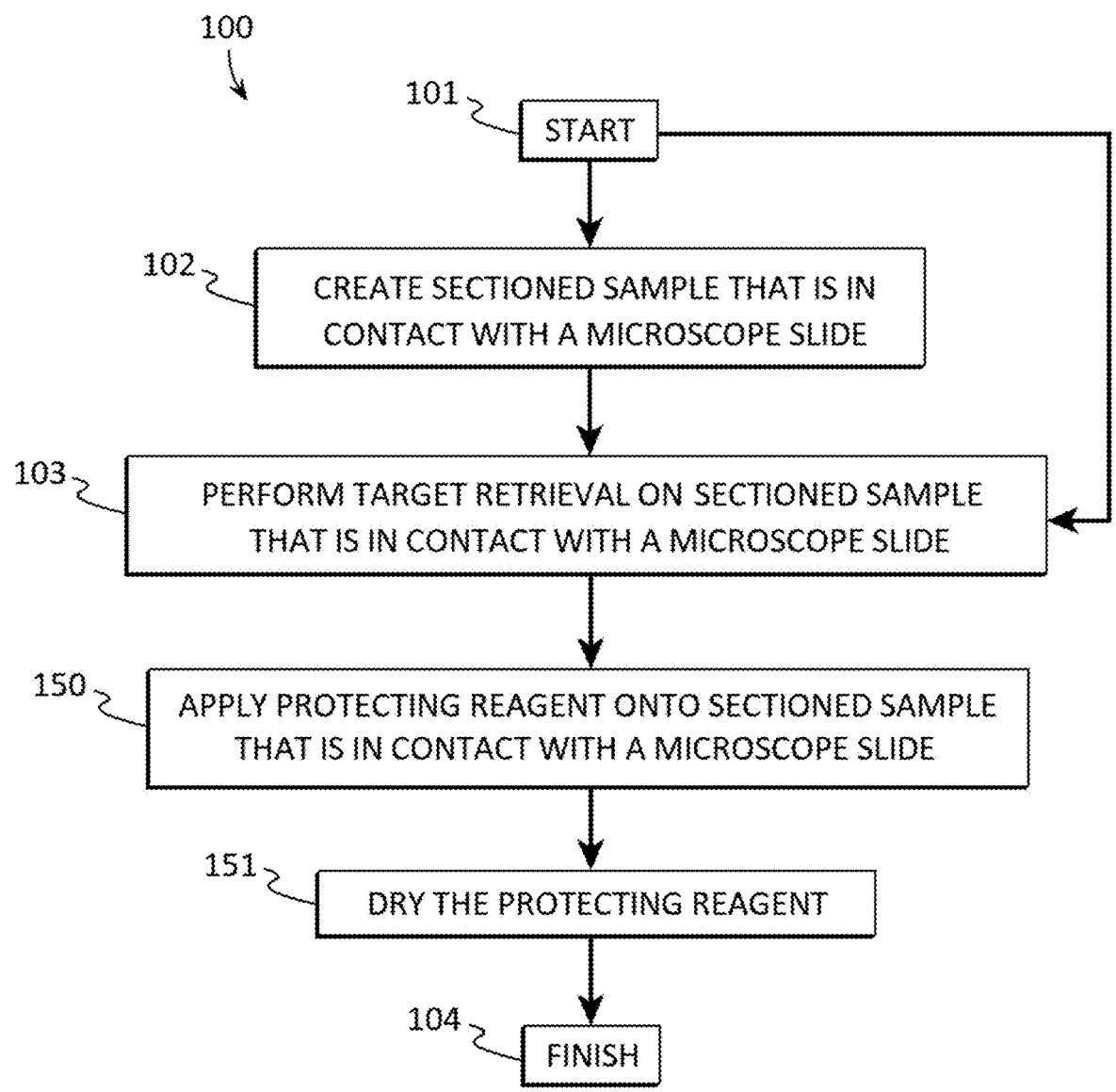
FIG. 1B-FIG. 1B depicts a block diagram of another example of a sample protection method according to various embodiments described herein.

The present invention will now be described by example and through referencing the appended figures representing preferred and alternative embodiments. FIGS. 1A and 1B illustrate examples of a sample protection method ("the method") 100 according to various embodiments. In some embodiments, the method 100 may be used to protect a biological sample (sometimes referred to as "the sample") on a microscope slide during target retrieval such that 1) the biological sample remains adhered to the microscope slide, and 2) the microscopic morphology of the biological sample remains intact. In some embodiments, the method 100 may be used to protect a biological sample (sometimes referred to as "the sample") on a microscope slide after target retrieval has been performed on the sample. It should be understood that the method 100 may be used for all biological samples regardless of whether they are tissue-based or cellular in origin.

Biological samples of cells and/or tissues are obtained for purposes of analyzing the biological constituents that comprise the sample. Sample analysis may be performed by methods of immunohistochemistry for analyzing protein components, or in situ hybridization for analyzing nucleic acid components. Prior to the analysis the sample must be prepared by appropriate methods. For example, a tissue biopsy may be removed from a patient and used as a biological sample for analysis.

The method 100 may start 101 and in some embodiments, the method 100 may include optional step 102 which may include creating a sectioned sample that is in contact with a microscope slide. Any suitable method for creating a sectioned sample that is in contact with a microscope slide may be used in step 102

In some embodiments, step 102 may comprise paraffin sample preparation by embedding the sample in paraffin which may comprise fixing the biological sample. Generally, biological samples containing cells or tissues are fixed to render them metabolically inactive and preserve molecular structures. In some embodiments, paraffin embedding sample preparation may utilize a fixative comprising formalin in aqueous solutions in order to fix the sample. In addition to formalin there are several fixative methods that can be used, such as alcohols, (methanol and ethanol), acetone, glutaraldehyde, and combinations thereof. Any suitable fixing method or composition may be used in paraffin embedding sample preparation.

After the sample has been fixed, the sample may then be dehydrated. Any suitable dehydrating method or composition may be used. For example, the sample may be dehydrated through a series of graded alcohols to remove all water.

After the sample has been dehydrated, the sample may be infused with embedding solvent, and any suitable embedding solvent infusing method or composition may be used. For example, the sample may be placed into a series of baths containing a paraffin solvent such as xylene (xylene being a solvent of the embedding media paraffin). The baths contain decreasing concentrations of alcohol and increasing concentrations of xylene. When the tissue is put through the final bath, the alcohol has been completely replaced with xylene.

Next, the sample may be embedded with a paraffin sectioning media so that the sectioning media may provide a firm surrounding matrix of the sample to support the sample during sectioning. Once the sample is infiltrated with xylene it can be embedded into a sectioning media of paraffin by placing the sample into heated paraffin that has been melted. The melted paraffin can now infiltrate the sample replacing the xylene. When cooled the paraffin solidifies to form a solid paraffin block containing the sample.

Next, the paraffin embedded sample may be sectioned via any suitable sectioning method or device to form a sectioned sample. For example, a microtome may be used to cut thin sections from the sample at approximately 4 to 6 microns thickness to produce one or more sectioned samples each having approximately 4 to 6 microns thickness. The thin sections containing the sectioned samples and the sectioning media or matrix are then applied to a microscope slide, and the thin sectioned sample becomes adherent to the microscope slide due to electrostatic interactions between the sample and the microscope slide.

Next, the sectioned sample may be de-embedded from the sectioning media via deparaffinization as the presence of paraffin inhibits the staining process. Paraffin can be removed by either heating the biological sample to melt the paraffin, or treating the biological sample with a paraffin solvent, such as xylene, to dissolve the paraffin.

The paraffin can be removed by heating the sample in an aqueous buffer. If the heating temperature is above the melting point of the paraffin (generally about 60 degrees Celsius), the paraffin will melt and be released into the heating fluid.

A more common method of deparaffinization involves submerging the microscope slide with the attached sample into a paraffin solvent, such as xylene. In this case the paraffin is dissolved into the paraffin solvent without the requirement for using an elevated temperature. This method avoids the use of elevated temperatures and is the method most commonly used. The melted or dissolved paraffin can then be removed by discarding the deparaffinizing solution leaving behind the deparaffinized sample. Following deparaffinization the sample is rehydrated into water or a suitable aqueous buffer.

Paraffin may be removed by many paraffin solvents. These solvents are generally categorized as apolar solvents and include xylenes, toluenes, naphthalenes and other related aromatic hydrocarbons, and citrus oils such as d-limonenes.

Methods of removing the paraffin by melting include a variety of mostly aqueous buffers and reagents. These methods have in common that they remove the paraffin by elevating the temperature of the reagent above the melting point of the paraffin. In some embodiments, heating methods of deparaffinization may be combined with the subsequent step 103 of heat induced antigen retrieval (target retrieval) such that these two steps are combined into a single step. It should be understood that any heating method of deparaffinization may be used.

Next, the sectioned sample may be rehydrated. In some embodiments, following deparaffinization, the sectioned sample may be rehydrated into water or a suitable aqueous buffer.

In some embodiments, step 102 may comprise freezing sample preparation in which the tissue of the sample is prepared and preserved through cryopreservation (freezing). Sample may be placed in an aqueous embedding medium, such as water or aqueous solution, and then frozen into a solid block of ice. This renders the sample sufficiently rigid that it can be sectioned into thin slices using a cryostat instrument and the thin slices may be placed onto microscope slide(s). Next, the sectioned sample may be heated to allow the ice sectioning media to melt to de-embed the section sample. The sectioned samples may then be fixed via any suitable fixing method or composition.

In some embodiments, step 102 may comprise resin sample preparation by embedding the sample in a resin, such as epoxy and acrylic resins. The recommended fixative for resin embedding is glutaraldehyde (4% in 0.1 M phosphate buffer). Like paraffin embedding, there follows a step-by-step process of dehydration (in alcohol) and then infiltration where the alcohol is replaced with resin. Glass or diamond knives are better suited to sectioning resin embedded material than steel knives as the edges are sharper. Dry sectioning is preferred for epoxy resin whilst wet is better for methacrylate. When cutting sections with a glass knife fitted with a trough, they will float directly on to the water and can be transferred to a pool of water upon a clean, glass slide. This in turn is placed on a hotplate set at 60 degrees Celsius to expand and dry the section. Hard resins provide a barrier to dyes and markedly reduced staining clarity. Removal of this type of resin is therefore recommended before staining. Epoxy resins can be degraded by alcoholic sodium hydroxide, potassium hydroxide, sodium methoxide or bromine vapour.

In some embodiments, and as shown in FIG. 1A, after a sectioned sample that is in contact with a microscope slide is created in step 102, the method 100 may proceed to step 150. In further embodiments, the method may skip step 102 and proceed to step 150. In further embodiments, and as shown in FIG. 1B, after a sectioned sample that is in contact with a microscope slide is created in step 102, the method 100 may proceed to step 103. In yet further embodiments, the method may skip step 102 and proceed to step 103.

It should be understood that steps 150 and 151 may be performed: before target retrieval is performed on a section sample; after target retrieval is performed on a section sample; and/or both before and after target retrieval is performed on a section sample.

It should also be understood that the method 100 may include step 102 of creating a sectioned sample that is in contact with a microscope slide or steps 150 and 103 of the method 100 may be performed on an already existing sectioned sample that is in contact with a microscope slide such as which may be created by any sectioned sample creating methods, such a which were described for step 102. For example, the method 100 may proceed from step 101 to step 150 (FIG. 1A), in which a protecting reagent onto a sectioned sample that is in contact with a microscope slide, whereby the pre-existing sectioned sample was created using paraffin sample preparation, freezing sample preparation, resin sample preparation, etc. As another example, the method 100 may proceed from step 101 to step 103 (FIG. 1B), in which target retrieval may be performed on a sectioned sample that is in contact with a microscope slide, whereby the pre-existing sectioned sample was created using paraffin sample preparation, freezing sample preparation, resin sample preparation, etc.

In step 150, a protecting reagent may be applied onto the sectioned sample so that all or portions of the sectioned sample and portions of the microscope slide that the sample is positioned on are covered by the protecting reagent. In some embodiments, a protecting reagent may comprise a water-soluble wax, which may include various Polyethylene Glycols (PEGs) and Methoxypolyethylene Glycols (MPEGs), such as the various CARBOWAX™ PEGs and CARBOWAX™ MPEGs offered by the Dow Chemical Company. Once the polyethylene glycol has dried over the sample it provides a waxy protective coating that protects the sample from detachment during heat-induced antigen retrieval. Because the waxy coating is water soluble, it is slowly solubilized and removed during the antigen-retrieval step, such that the wax has been entirely removed by the end of the antigen-retrieval procedure. In some embodiments, a protecting reagent may comprise a water-soluble polymer, such as polyvinyl alcohol, polyvinylpyrollidone, alginic acid, and carrageenan. Any water-soluble polymer and/or wax that can be subsequently removed with water and does not interfere with staining may be used in step 150. In further embodiments, a protecting reagent may comprise a solution of between approximately 1.0 to 99.99 percent, and more preferably between approximately 1.0 to 10.0 percent, water-soluble wax dissolved in water. In still further embodiments, a protecting reagent may comprise a solution of between approximately 1.0 to 99.99 percent, and more preferably between approximately 1.0 to 10.0 percent, water-soluble polymer dissolved in water.

In step 151, the protecting agent may be dried. Once the protecting agent has dried over the sample it provides a waxy protective coating that protects the sample from detachment from the microscope slide during target retrieval. Any suitable drying method may be used, including heat and/or time. For example, the slides having a sectioned sample and protecting agent may be dried for 2 hours at 37 C until all of the protecting reagent had dried, thus leaving a protective layer on top of the sample.

In some embodiments, and as shown in FIG. 1A, after step 151, target retrieval may be performed on the sectioned sample in step 103. In further embodiments, and as shown in FIG. 1B, steps 150 and 151 may be performed after target retrieval of step 103. The biological samples thus prepared generally cannot be stained until the targets have been retrieved. For purposes of this specification, unless otherwise noted, the terms antigen-retrieval, epitope-retrieval, and target-retrieval are interchangeable, and will be referred to collectively as antigen retrieval.

In some embodiments, target retrieval may comprise heat-induced antigen retrieval. During the preceding fixation process, and in particular fixation with formalin, the proteins and nucleic acids become denatured and cross-linked, such that the targets are hidden from subsequent binding by an appropriate probe or antibody. The biological samples must then be treated with heat during a process called Heat-Induced Target Retrieval if they are to be subsequently stained by Immunohistochemistry or In Situ Hybridization. In the case of Immunohistochemistry, the more specific term of Heat-Induced Antigen Retrieval is frequently used.

As shown in FIG. 2, fixation of sample causes antigens (A) within the proteins 201 to be masked. Heating of sample causes protein 201 to unfold. Subsequent cooling of sample causes protein 201 to refold, leaving antigens (A) unmasked.

The targets may be studied by applying various staining methods to the samples that render the targets visible by microscopic analysis. Some methods of staining targets include immunohistochemistry (IHC), Immunocytochemistry (ICC) and In Situ Hybridization (ISH). IHC is used to study tissues whereas ICC is used to study collections of individual cells. Both of these methods are similar with the main difference being the source of the biological sample. For simplicity this specification will refer to both methods simply as IHC. Each of the staining methods requires that the targets undergo a process whereby their molecular structure is altered to render them detectable. In the case of IHC this process is known as Antigen Retrieval because the targets are known as antigens. In the case of the ISH method of staining, the targets are known as nucleic acids. Strictly speaking nucleic acid targets are not antigens. However, for simplicity this specification will refer to the retrieval of all targets simply as target retrieval or sometimes as antigen retrieval.

Figure 4:
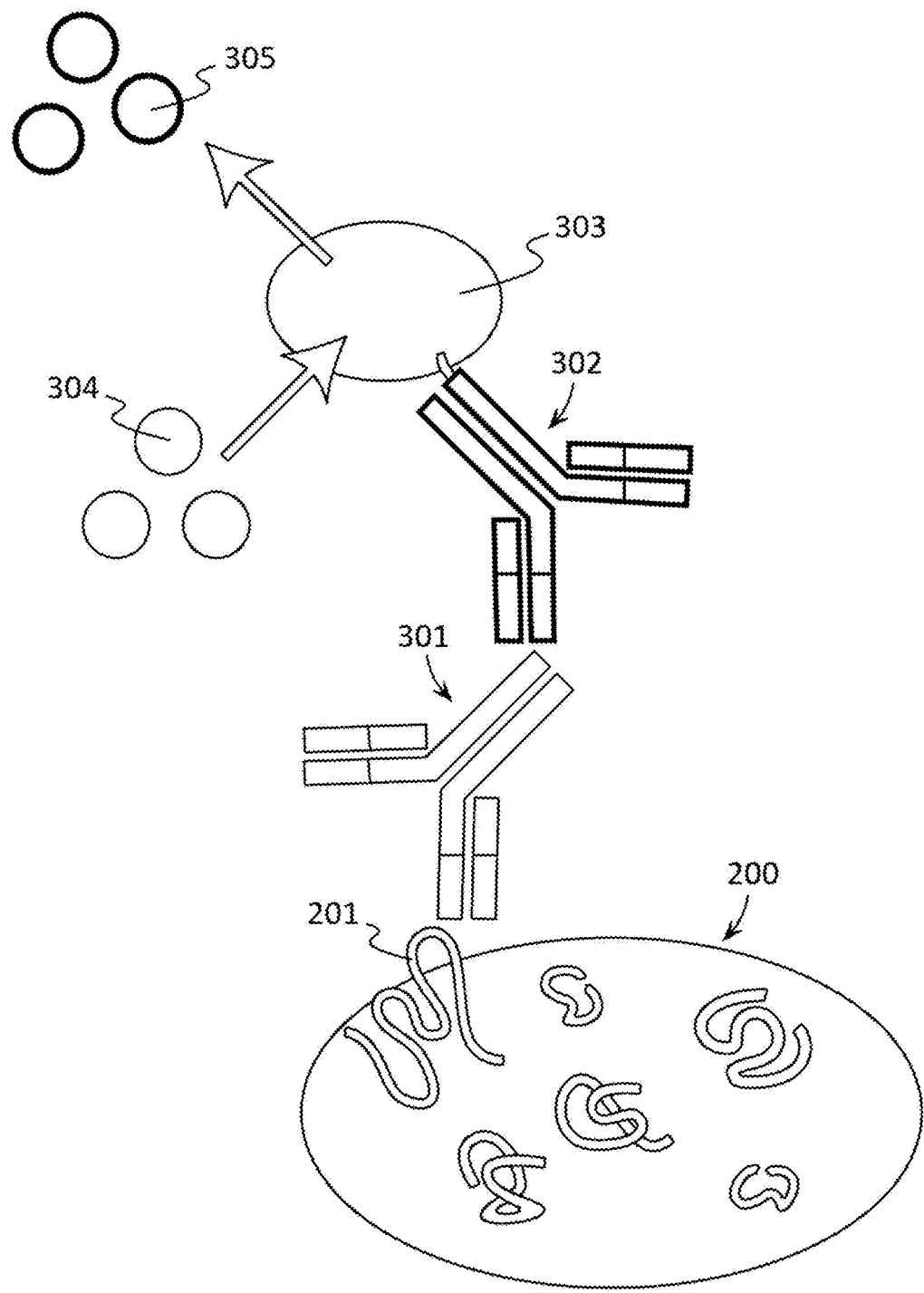
FIG. 4-FIG. 4 depicts a schematic view of an example of immunohistochemistry staining according to various embodiments described herein.

An example of Immunohistochemistry staining is shown in FIG. 4 in which primary 301 and secondary 302 antibodies are used to visually indicate the presence of a desired protein 201 of a fixed cell tissue 200 of a sectioned sample using an enzyme 303, such as peroxidase or alkaline phosphatase, which turns a chromogen 304 into a colored product 305.

Antigen retrieval is a process of treating a biological sample to retrieve antigens prior to staining, such that they become detectable by IHC staining. In IHC staining, a first antibody is applied to a sample and binds to the molecule of interest if present. If the molecule of interest is not present no binding occurs. It is this binding event that determines the presence of absence of the molecule of interest. The molecule of interest is termed an antigen. During the process of preparing a sample for IHC staining, the sample may be subjected to a fixative solution. The fixative solution halts all metabolic activity in the sample and immobilizes the molecular structure by creating chemical links within the molecular structure. Such links help maintain the molecular structure during staining and analysis. However, such cross-links may also alter the molecular structure in such a way that antibodies can no longer bind to their antigen. In this case the antigen is referred to as denatured. Denatured antigens cannot be stained by IHC, and they must first be retrieved and restored to their native configuration. The process of antigen retrieval is intended to retrieve antigens such that they become detectable by IHC staining.

There are generally two preferred method for target retrieval or antigen retrieval. The first method is termed Enzyme Antigen Retrieval. In this method a proteolytic enzyme is applied to the biological sample and is allowed to moderately digest the protein structures such that the molecular cross-links are broken and the antigens are restored to a more natural configuration. The method of Enzyme Antigen Retrieval is poorly understood and it is not clear why this method works for some antigens but not for others. Some examples of proteolytic enzymes that have been shown to work for Enzyme Antigen Retrieval include pepsin, papain, trypsin, Proteinase K, Protease Type XXIV, and chymotrypsin. Enzyme Antigen Retrieval with proteolytic enzymes is rarely performed anymore because it has been shown that Heat Antigen Retrieval is generally superior. When performed the samples are submerged in enzyme solution at a temperature of about 20 to 37 degrees Celsius, and allowed to incubate in this solution for approximately 5 to 10 minutes. The samples are then rinsed in buffer to complete the Enzyme Antigen Retrieval step.

The second form of Antigen Retrieval is Heat-Induced Antigen Retrieval. In this method the biological samples are heated to a temperature of approximately 90 to 125 degrees Celsius, in an aqueous Antigen Retrieval solution. The heating of the sample results in the breaking of the cross-links, thus restoring the antigens to a more natural configuration.

First the slides are deparaffinized and rehydrated as described above. Next the samples are submerged into an Antigen Retrieval solution.

Figure 3:
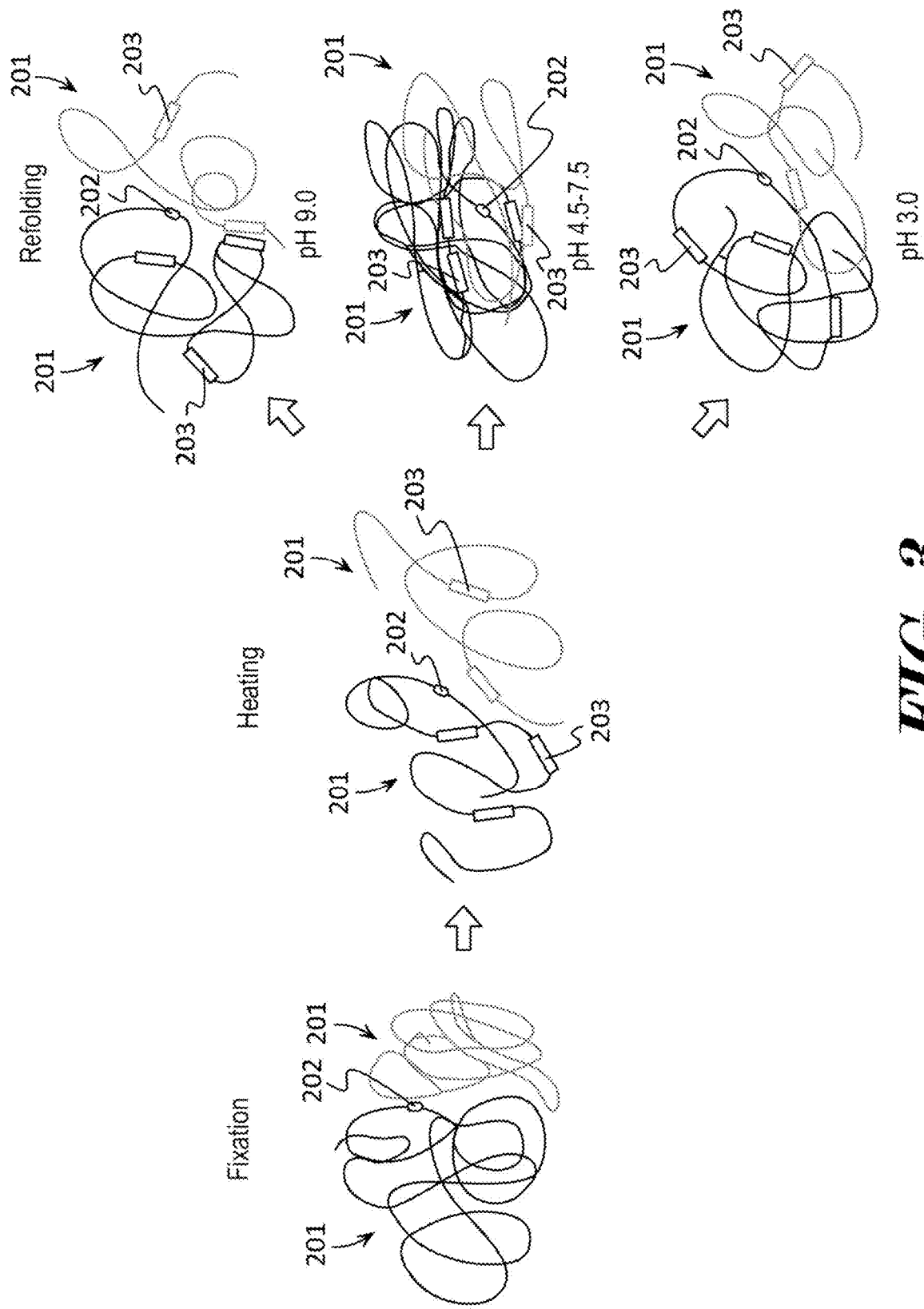
FIG. 3-FIG. 3 shows a block diagram of refolding of protein after heat-induced antigen retrieval according to various embodiments described herein.

FIG. 3 shows an example of refolding of protein 201, having epitope 202 and hydrophobic regions 203, after heat-induced antigen retrieval. Following heating, protein 201 refolds during cooling phase. Final configuration of refolding is controlled by pH of antigen retrieval solution during refolding process. Heat-Induced Target Retrieval can be performed with microwave ovens, pressure cookers, vegetable steamers, autoclaves, or water baths. Heat-Induced Target Retrieval is time, temperature, buffer, and pH-sensitive. Heat-Induced Target Retrieval may be defined in the simplest terms as the use of heat coupled with specific buffered solutions to recover antigen reactivity in formalin fixed paraffin embedded tissue. A wide range of buffered solutions have been employed for Heat-Induced Target Retrieval. Currently, Heat-Induced Target Retrieval solutions can be grouped in three categories based on pH and buffer compositions:

Low pH (pH~3-5) solutions frequently buffered by glycine-HCl.

Low to neutral pH (pH~6-7) solution buffered with citric acid.

High pH (pH~8-10) buffered by Tris or EDTA.

Example antigen retrieval solutions include those sold by Sigma-Aldrich, Inc., such as: Product No. C9999 Citrate Buffer, pH 6.0, 10×, Antigen Retriever; Product No. E1161 EDTA Buffer, pH 8.5, 10×, Antigen Retriever; Product No. H3292 Histo/Zyme, pH 7.2, Ready to Use, Antigen Retriever; Product No. R2283 Pepsin Reagent, Ready to Use, Antigen Retriever; and Product No. T6455 Tris-HCl Buffer, pH 10, 10×, Antigen Retriever.

The pH of the antigen retrieval solution also influences sample adherence. Basic antigen retrieval solutions (pH 8 to 9) are more prone to causing sample detachment compared to the neutral or acidic antigen retrieval solutions. While the method 100 may be used with any antigen retrieval solution, preferably, the method 100 may be used with antigen retrieval solutions having a pH that is greater than 7.0.

Heat-Induced Antigen Retrieval is the preferred method because of its superiority over Enzyme Antigen Retrieval.

One of the main drawbacks to Heat-Induced Antigen Retrieval is that the sample may become partially or completely detached from the microscope slide. In such cases the sample may be lost and cannot be further analyzed. Furthermore, even if the sample is not entirely detached from the microscope slide, it may be degraded in such a way that the microscopic morphology if the tissue is damaged compromising subsequent microscopic examination.

The method 100 of present invention overcomes these limitations by providing a method for protecting the sample to prevent sample detachment from a microscope slide during target retrieval, such as during a heating phase, and/or after target retrieval. In some embodiments, after a sectioned sample is created in step 102, and prior to heat induced antigen retrieval which may be performed in step 103, the sample may be treated to render it firmly attached to the microscope slide. The steps of this method 100 may include: removing the deparaffinized microscope slide and attached sample from an aqueous solution, such as water or buffer; orienting the microscope slide and attached sample horizontally, and while still wet, applying a few drops of a protecting reagent in step 150, in which the protecting reagent may be composed of a water-soluble polymer dissolved in water such that the sample is completely covered with the protecting reagent; allowing the protecting reagent to dry over the sample in step 151. Once the protecting reagent has dried and formed a protecting layer over the sample in step 151, the sample can then be processed by heat-induced antigen retrieval without the sample detaching from the microscope slide during the antigen retrieval or target retrieval process.

In some embodiments, after steps 103 (FIG. 1A) and/or 151 (FIG. 1B), the method 100 may finish 104.

Example Operation of a Preferred Embodiment

The IHC staining process can be broken down into parts, and each part can be further broken down into steps.

The first part of IHC involves preparing a biological sample for investigation, such as a tissue suspected of having some disease. An example would be a tissue biopsy of a suspected cancer lesion. The biopsy may then be studied to see if it contains a particular molecular marker, or target of interest. If the target of interest is present in the biopsy then the diagnosis of cancer is confirmed, whereas if the target of interest is not present in the biopsy then the diagnosis of cancer may be ruled out. In the IHC staining method the target of interest is an antigen.

Preparation of a Biological Sample for Histological Examination

1. A tissue sample is obtained and placed into fixative.

2. After fixation the tissue is dehydrated through a series of graded alcohols to remove all water.

3. After dehydration the tissue is placed into a series of baths containing a paraffin solvent such as xylene. The baths contain decreasing concentrations of alcohol and increasing concentrations of xylene. When the tissue reaches the final bath the alcohol has been completely replaced with xylene and the sample has been infused with embedding solvent.

4. Once the tissue is infiltrated with xylene it can be embedded into paraffin by placing the tissue into heated paraffin that has been melted. The melted paraffin can now infiltrate the tissue replacing the xylene in.

5. When cooled the paraffin solidifies to form a solid paraffin block containing the tissue.

6. The paraffin block containing the tissue can be cut into thin slices of approximately 4 u, and some of the cut sections are attached to a microscope slide in preparation for staining and microscopic analysis.

The steps described above for preparation of a biological sample are standard histochemical methods that precede many different types of histological analysis.

Preparation of a Biological Sample on a Microscope Slide for IHC Staining

1. The paraffin is removed from the sample by a process called deparaffinization.

2. The paraffin is replaced in the tissue with an aqueous solution, called rehydration to complete step 102.

Sample Protection Steps 150 and 151

The next step in the immunohistochemistry method would normally include heating the sample to a high temperature (equal to or greater than 100 C) commonly referred to as heat-induced antigen retrieval. However, the method 100 of the present invention differs from existing methods as, in some embodiments, the method 100 first applies a sample protection reagent in order to protect the sample from heat-induced damage, such as sample detachment and or degradation of sample morphology in step 150, and also allows the sample protection reagent to dry onto the sectioned sample in step 151.

Example 1. Antigen Retrieval Procedure

A deparaffinized and rehydrated sample on a microscope slide was laid horizontally on a flat surface and 200 ul of a protecting solution was applied over the sample in step 150. The slides were then dried for 2 hours at 37 C until all of the protecting reagent had dried, thus leaving a protective layer on top of the sample in step 151.

In step 111, the samples thus prepared were then placed into a Coplin jar containing 50 ml of antigen retrieval solution for target retrieval. The antigen retrieval solution was composed of a 0.5M Tris plus and 0.5M EDTA in water at a pH of 9.0.

The Coplin jars were then placed into a pressure cooker and heated to a temperature of 120 C, at 15 psi, for 15 minutes. After 15 minutes the Coplin jars were allowed to cool inside the pressure cooker for an additional 20 minutes prior to removal from the pressure cooker.

Example 2. Immunohistochemistry Procedure

After heat-induced antigen retrieval the slides were stained by immunohistochemistry using antibodies for Cytokeratiin AE1/AE3 and CD20 (Diagnostic BioSystems, Pleasanton, Calif.) and detected with a peroxidase staining method (Diagnostic BioSystems) according to the manufacturer's instructions.

Slides were then counterstained with hematoxylin and mounted with a permanent mounting medium and coverslipped prior to microscopic examination.

Microscopic examination evaluated the following parameter:

1. Tissue adherence to the microscope slide graded as a percent of tissue remaining intact on the microscope slide.

2. Immunohistochemistry staining results graded on a scale of 0-3 with 0=no staining, 1=weak staining, 2=moderate staining, and 3=strong staining.

Example 3. Protecting Reagents composed of Polyethylene glycol (PEG)

The following PEG solutions were tested and compared to a control sample that was not protected with PEG as shown in Table 1 below.

TABLE 1

Example Protecting Reagents composed of Polyethylene glycol (PEG):

| Polymer | Molecular Weight | Percent (w/v) in water |
| --- | --- | --- |
| 1. PEG | 3350 | 2.5% |
| 2. PEG | 20,000 | 2.5% |
| 3. PEG | 3350 | 5% |
| 4. PEG | 20,000 | 5% |

Results are shown in Table 2 below.

TABLE 2

Tissue Detachment Results of Example Protecting Reagents composed of Polyethylene glycol (PEG) of Table 1:

| Protecting Reagent | Staining: AE1/AE3 | Staining: Vimentin | % Tissue detachment |
| --- | --- | --- | --- |
| None | 3.0 | 3.0 | 75% |
| PEG 3350, 2.5% | 3.0 | 3.0 | 25% |
| PEG 20,000 2.5% | 3.0 | 3.0 | 30% |
| PEG 3350, 5.0% | 3.5 | 3.5 | 20% |
| PEG 20,000, 5.0% | 3.0 | 3.0 | 20% |

As can be seen in Table 2, tissue detachment is much less for samples treated with a protecting reagent.

Example 4. Protecting Reagents Composed on Alginic Acid

Alginic acid is a water-soluble polymer. A solution of Alginic acid in water may be treated with Calcium, such as calcium chloride, to form a water-insoluble polymer gel. The gel will remain stable in water and will not dissolve. Addition of a calcium chelating agent such as EDTA or citric acid will remove the calcium from the alginic acid gel, thus causing the gel to re-dissolve.

The use of Alginic acid as a protecting reagent, either with or without calcium gelling, was tested as a protective layer to coat samples prior to heat-induced antigen retrieval.

After deparaffinization and rehydration, the samples were covered with protecting reagent comprising a solution of alginic acid in water. Samples that were not treated with calcium were allowed to dry for 2 hours at 37 C. This formed a dried protective layer of alginic acid over the sample.

For calcium treatment the slides with the attached tissue samples were first covered with a solution of alginic acid dissolved in water. The alginic acid was allowed to incubate on the slide for 10 minutes. The slides were then exposed to a solution of Calcium chloride, which caused the alginic acid to form a gel. The slides were then dried for 2 hours at 37 C. The polymer conditions tested are shown in Table 3 below.

TABLE 3

Example Protecting Reagents composed of Alginic acid:

| Polymer | Percent (w/v) in water |
| --- | --- |
| 1. Alginic acid | 2.5% |
| 2. Alginic acid | 5.0% |
| 3. Alginic acid | 2.5% + 0.5M $CaCl_2$ |
| 4. Alginic acid | 5.0% + 0.5M $CaCl_2$ |

Results are shown in Table 4 below.

TABLE 4

Tissue Detachment Results of Example Protecting Reagents composed of Alginic acid of Table 3:

| Protecting Reagent | Staining: AE1/AE3 | Staining: Vimentin | % Tissue detachment |
| --- | --- | --- | --- |
| None | 3.0 | 3.0 | 85% |
| Alginic acid, 2.5% | 3.0 | 3.0 | 35% |
| Alginic acid 5.0% | 3.0 | 3.0 | 25% |
| Alginic acid 2.5% + $CaCl_2$ | 3.0 | 3.0 | 20% |
| Alginic acid 5.0% + $CaCl_2$ | 3.0 | 3.0 | 15% |

As can be seen in Table 4, tissue detachment is much less for samples treated with a protecting reagent.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A sample protection method for reducing detachment of a sectioned sample from a microscope slide during target retrieval performed on the sectioned sample, the method comprising the steps performed in the following sequential order:
    applying a protecting reagent onto the sectioned sample that is in contact with the microscope slide, the sectioned sample having been removed from an embedding medium;
    drying the protecting reagent; and
    performing target retrieval on the sectioned sample,
    wherein the protecting reagent is polyethylene glycol or alginic acid,
    wherein the target retrieval comprises heat-induced antigen retrieval, and
    wherein detachment of the sectioned sample is reduced during heat-induced antigen retrieval.

2. The method of claim 1, wherein the sectioned sample was created using paraffin sample preparation.

3. The method of claim 1, wherein the sectioned sample was created using a sample preparation selected from the group consisting of freezing sample preparation and resin sample preparation.

4. The method of claim 1, wherein the protecting reagent is dissolved in water.

5. The method of claim 1, wherein the target retrieval comprises the use of an antigen-retrieval solution.

6. The method of claim 5, wherein the antigen-retrieval solution comprises a pH greater than 7.

7. A sample protection method for reducing detachment of a sectioned sample from a microscope slide during target retrieval performed on the sectioned sample, the method comprising the steps performed in the following sequential order:
    embedding a sample in an embedding medium;
    sectioning the sample and placing a section of the sample in contact with a microscope slide to produce the sectioned sample;
    removing the sectioned sample from the embedding medium;
    applying a protecting reagent onto the sectioned sample;
    drying the protecting reagent; and
    performing target retrieval on a sectioned sample in contact with a microscope slide,
    wherein the protecting reagent is polyethylene glycol or alginic acid,
    wherein the target retrieval comprises heat-induced antigen retrieval, and
    wherein detachment of the sectioned sample is reduced during heat-induced antigen retrieval.

8. The method of claim 7, wherein the protecting reagent is dissolved in water.

9. The method of claim 7, wherein the target retrieval comprises the use of an antigen-retrieval solution.

10. The method of claim 9, wherein the antigen-retrieval solution comprises a pH greater than 7.

* * * * *